United States Patent [19]
Johnson

[11] Patent Number: 5,621,163
[45] Date of Patent: Apr. 15, 1997

[54] APPARATUS FOR TESTING RESIN FLOW

[76] Inventor: David H. Johnson, 7060 Koll Center Pkwy., Ste. 316, Pleasanton, Calif. 94566

[21] Appl. No.: 580,073

[22] Filed: Dec. 20, 1995

[51] Int. Cl.⁶ .......................... G01N 15/08; G01N 33/44
[52] U.S. Cl. ................................ 73/38; 73/53.01
[58] Field of Search ............................ 73/37, 38, 54.13, 73/54.14, 54.11, 53.01

*Primary Examiner*—Michael Brock
*Attorney, Agent, or Firm*—Bielen, Peterson & Lampe

[57] ABSTRACT

An apparatus for testing the flow of liquid resin through a solid porous material utilizing a tube of a certain cross-sectional size. The tube includes first and second openings and is intended to carry the liquid resin. A vessel is also employed, having an interior chamber and an opening for accommodating a portion of the tube within the chamber of the vessel. A reservoir for the resin is located within the chamber and communicates with the first opening of the tube within the chamber. Pressure means is exerted in the chamber to urge the liquid resin through the tube. A mass of the solid porous material is placed within the tube between the reservoir and the tube second openings. Penetration or flow during a set time period, through the material is measured as a distance relative to the position of the material located in the tube.

12 Claims, 2 Drawing Sheets

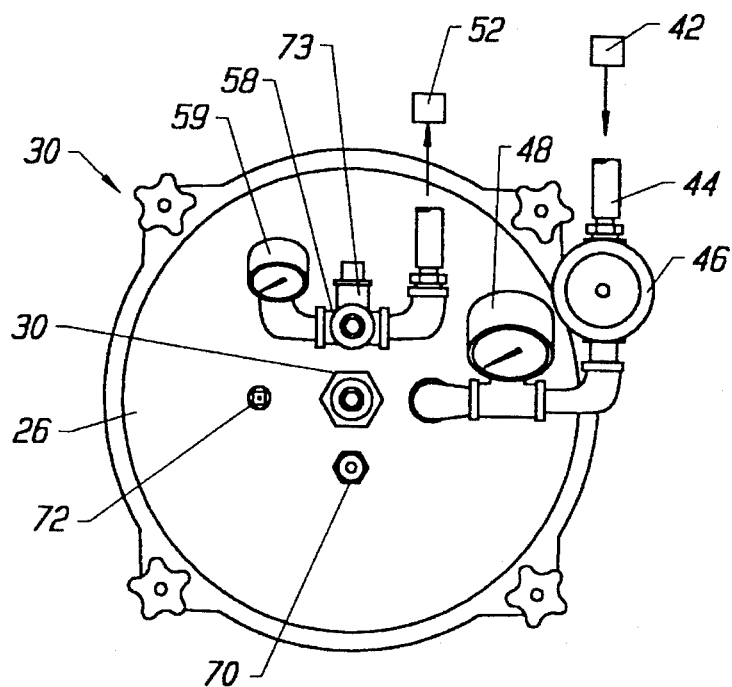
FIG. 2
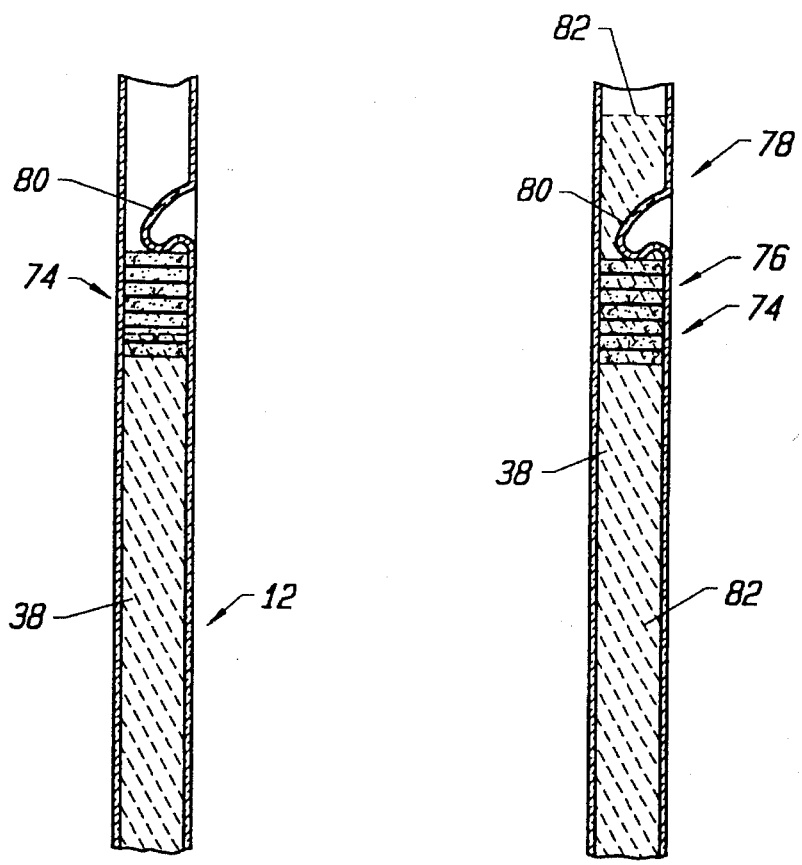
FIG. 3
FIG. 4

APPARATUS FOR TESTING RESIN FLOW

BACKGROUND OF THE INVENTION

Pipes are employed throughout the world to carry flowable materials such as fuel, sewage, water, industrial components, and the like. To avoid replacement of pipes, especially those that are located underground, systems have been developed to reline such pipes using sleeves of material that can be eventually hardened by polymerization of a chemical resin impregnated into a polymeric sleeve. It is important that the resin employed penetrates or "wet" through the sleeve of material within a certain time in order to produce a lining that does not have voids or gaps and/or to minimize labor costs.

In the past, liquid resins have been employed based on specifications and experience as to such resin's ability to wet or penetrate the absorbent material. Unfortunately, the lining material and liquid resin interaction does not always proceed according to predictions. Thus, it is necessary to pre-determine the flow of liquid resin through the lining fabric prior to its use.

An apparatus and method to pre-test liquid resins with respect to penetration of a lining material would be a notable advance in the industrial arts.

SUMMARY OF THE INVENTION

In accordance with the present invention, an apparatus and method for testing resin flow through a solid porous lining material is herein provided.

The apparatus of the present invention includes a tube of a certain cross-sectional size for carrying the resin. The tube includes first and second openings on opposite ends thereof. The tube may be formed of rigid or semi-rigid material and is preferably transparent to view movement of the resin therewithin.

In addition, the apparatus of the present invention is provided with a vessel having an interior chamber. The vessel includes an opening for the tube to permit the tube first opening to lie within the chamber of the vessel. In addition, the second opening of the tube would lie outside the chamber for viewing and access. The vessel is provided with a door or lid and is sealable in order to apply a certain pressure to the interior chamber of the vessel. In this regard, openings may be present in the vessel to install pressure gages, vacuum gages, and the like in order to determine the conditions within the vessel during use.

A reservoir for the resin is also found in the present invention and is located within the vessel chamber. The tube first opening extends into the vessel chamber and communicates with the resin in the reservoir. Thus, the liquid resin is free to flow from the reservoir through the first opening of the tube and out of the chamber.

Pressure means urges the resin from the reservoir, along the tube, and toward the second opening of the tube outside the chamber. Such a pressure means may take the form of a pressure source which creates an over-pressure in the chamber. In addition, a vacuum source may be attached to the second opening of the tube to create a pulling effect on the resin flowing from the tube.

A mass of the solid, porous, lining, material is placed within the tube between the reservoir and the tube second opening. Normally, the mass of the solid porous material is viewable through the tube and may take the form of a plurality of wafers or disks of the solid materials stacked atop one another. Moreover, stop means may be employed in the tube to prevent movement of the mass of the solid porous material upwardly or downwardly during the testing procedure. Such stop means may take the form of a detent in the tube, an obstruction extending into the interior of the tube, a narrowing of the tube wall, the forming of a friction surface near the mass of solid porous material, and the like.

In any case, the pressure applied to the chamber and the vacuum applied to the second opening of the tube is of a predetermined value. In addition, the application of the pressure means takes place during a certain time period. Likewise, the liquid resin may be set at a certain temperature. Maintaining these parameters of pressure, resin temperature, and time produces comparative results of the penetration of the resin through the mass of the solid porous material found within the tube. Moreover, the resin may be allowed to harden after initiation of the urging of the resin through the tube and against and through the mass of solid porous material, in order to create a permanent record of the penetration characteristics of the resin relative to the mass of the solid porous material.

It may be apparent that a novel and useful apparatus and method for determining resin flow across or through a solid porous material has been hereinabove described.

It is therefore an object of the present invention to provide an apparatus and method for determining resin flow through a solid porous material which is accurate and applicable to determining the integrity of linings of conduits and pipes.

It is another object of the present invention to provide an apparatus and method for determining resin flow through a solid porous material which is capable of determining variations of interaction between a resin and a lining material for pipes and conduits.

Yet another object of the present invention is to provide an apparatus and method for determining resin flow through a solid porous material which is simple and portable.

Another object of the present invention is to provide an apparatus and method for determining resin flow through a solid porous material used in lining pipes which determines the time for penetration of a resin and results in decreased cost in relining pipes and conduits.

Another object of the present invention is to provide an apparatus for determining resin flow through a solid porous material which is particularly useful in lining pipes of large diameters and wall thicknesses.

The invention possesses other objects and advantages especially as concerns particular characteristics and features thereof which will become apparent as the specification continues.

BRIEF DESCRIPTION OF THE DRAWINGS

FIG. 2 is a generally top plan view of the apparatus of the present invention taken along line 2—2 of FIG. 1

FIG. 3 is a sectional view of the tube depicting resin in contact with wafers of the solid porous material held therein.

FIG. 4 is a sectional view of the tube carrying the liquid resin in which the resin has penetrated and passed through the mass of solid porous material held within the tube.

Figure 1:
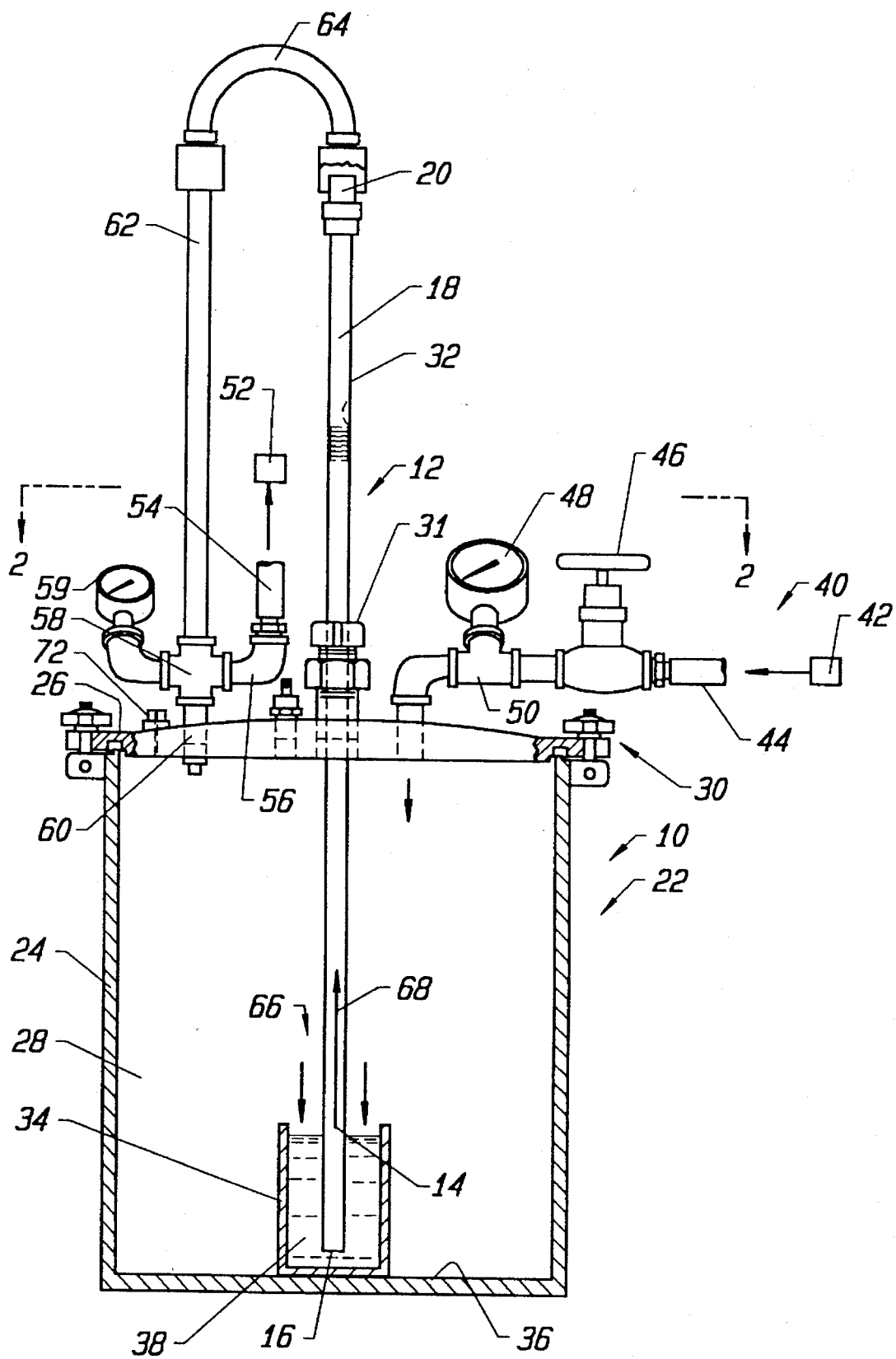
FIG. 1 is a front elevational view of the apparatus of the present invention showing the pressure vessel and a resin reservoir in section, with fittings on the lid being rotated for clarity from the position shown in FIG. 2.

For a better understanding of the invention reference is made to the following detailed description of the preferred embodiments thereof which should be referenced to the prior described drawings.

DETAILED DESCRIPTION OF THE PREFERRED EMBODIMENTS

Various aspects of the present invention will evolve from the following detailed description of the preferred embodiments thereof which should be taken in conjunction with the prior described drawings.

The invention as a whole is depicted in the drawings by reference character 10. The apparatus 10 for determining liquid resin flow includes as one of its elements a tube 12 of a predetermined cross-sectional size. Tube 12 may be of any suitable size, but is between 11 and 12 millimeters in diameter in the embodiment shown in FIG. 1. Tube 12 may be constructed of material such as metal, but is preferably formed of translucent glass or plastic in order to view the items found within tube 12. Tube 12 includes a first end portion 14 having an opening 16 and a second end portion 18 having an opening 20.

Vessel 22 is also found in the present invention. Vessel 22 is capable of holding a pressure and includes a generally cylindrical base 24 and a removable lid 26. A plurality of threaded fittings 30 hold lid 26 in place when a pressure is found within chamber 28 of vessel 22. Tube 12 first end portion 14 extends into chamber 28 of vessel 22 while second end portion 18 lies upright and outside of chamber 28 of vessel 22. Seal fitting 31 seals the interconnection between pressure chamber 28 and the outside wall 32 of tube 12. Lid 26 serves as a support for various fittings depicted in FIGS. 1 and 2. It should be noted that the arrangement of such fittings, which will be described hereinafter, in FIG. 1 have been rotated slightly for the sake of clarity from the positions shown in FIG. 2.

Reservoir 34 is also an element of the present invention and is located on base 24 in chamber 28 of vessel 22. Reservoir 34 is filled with a particular liquid resin 38 which is capable of communicating with opening 16 of tube 12.

Pressure means 40 is also depicted in the drawings for urging resin 38 from reservoir 34, along the interior of tube 12, and toward second opening 20 of tube 12. Pressure means 40 may include a source of positive pressure 42 which may be a pneumatic pump. Pneumatic pressure travels through conduit 44, valve 46, and into chamber 28 of vessel 22. Valve 46 may also take the form of a pressure regulator. Gage 48 indicates the value of the pressure within tee 50.

Likewise, pressure means 40 may also include a source of negative pressure or vacuum 52 which may emanate from a vacuum pump. The vacuum is drawn through conduit 54, elbow 56, manifold 58, pipe 62, conduit 64, and tube 12. Gage 59 indicates the vacuum within manifold 58. Pipe 62 connects to the second opening of tube 20 via flexible conduit 64. Manifold 58 is held to lid 26 by fitting 60, which sealingly engages lid 26. Thus, liquid resin 38 is pressured into opening 16, directional arrows 66 by positive pressure source 42. At the same time, vacuum source 52 tends to pull liquid resin 38 through tube 12 toward second opening 20. Liquid resin 38 tends to move along directional arrow 68 through tube 12.

Turning to FIG. 2, the pressure relief valve 70 opens if the pressure within chamber 28 is beyond a pre-set value. Pressure bleed plug 72 aids in the regulation of the pressure within vessel 22 when pressure source 42 is operating. In addition, vacuum regulator 73 automatically maintains the vacuum level in second end portion 18 of tube 12. Typically, pressure gage 48 reads 30 inches of water, while vacuum gage 59 reads 25 inches of mercury.

A mass 74 of the material being tested in conjunction with resin 38 for penetration or "wet out" characteristics is placed within tube 12. For example, mass 74 may be composed of a polyester teraphthalic felt of selected fineness, available from Insituform Technologies, Inc. of Memphis, Tenn., a typical pipe lining material. Mass 74 may take the form of a plurality of disks or wafers 76 stacked one atop another. Stop means 78 prevents the movement of plurality of disks upwardly toward opening 20. Stop means 78 takes the form of a detent or dimple 80 which restricts the passage of disks 76 through the interior 82 of resin 38.

In operation, tube 12 is placed through lid 26 such that first end portion 14 extends within chamber 28 of vessel 22. The first opening 16 of tube 12 is placed within reservoir 34 containing a particular liquid resin 38 to be tested therewithin. Lid 26 is then tightened and sealed against base portion 28 of vessel 22 by plurality of fittings 30. Positive pressure source 42 and vacuum source 52 are then applied to chamber 22. Valve 46 regulates the positive pressure in vessel chamber 28. Also, vacuum regulator 73 regulates the vacuum "pull" on upper portion 18 of tube 12. Gages 48 and 59 indicate the value of the positive pressure and vacuum pressure applied, respectively. Plug 72, communicating with chamber 28, bleeds air from vessel 22 to adjust the desired pressure within chamber 28 according to gage 48. The liquid resin 38 then moves upwardly within tube 12 and into contact with mass 74 of the solid porous material being tested. The penetration test using apparatus 10 is conducted for a certain time period. It should be noted that mass 74 is also used in lining pipes as the matrix for resin 38. FIG. 3 indicates resin 38 as just beginning to contact mass 74 and not penetrating all of the plurality of disks therein. FIG. 4 represents resin 38 having penetrated all of the plurality of disks 76 and rising to a level 82 above mass 74. FIG. 4 indicates acceptable penetration by resin 38 under controlled conditions while FIG. 3 represents unacceptable penetration of resin 38 relative to mass 74. Liquid resin 38 may be allowed to harden in tube 12 to provide a permanent record of penetration or "wet out" of mass 74. When the test is complete, bleed plug 72 permits the pressure in chamber 28 to equalize to atmospheric pressure allowing lid 26 to be easily removed.

While in the foregoing, embodiments of the present invention have been set forth in considerable detail for the purposes of making a complete disclosure of the invention, it may be apparent to those of skill in the art that numerous changes may be made in such details without departing from the spirit and principles of the invention.

The following example is included for the purpose of illustration, but is not intended to limit the scope of the invention unless otherwise indicated

EXAMPLE 1

Four (4) resins were tested for relative penetration or "wet out" rate of pipe lining felt using the apparatus shown in FIGS. 1–4 hereinabove. The tests were conducted at a pressure within vessel 22 of 30 inches of water, per gage 48, and a vacuum of 25 inches of mercury, per gage 59, and at varying temperatures. The temperature of the liquid resin was measured in reservoir 34 immediately before placement in vessel 22. A pyrex tube containing 10 cylindrical disks of felt of the polyester teraphthalic felt material were stacked one on top of another such that the top of the stack lay at 302 millimeters from the first opening 16 of the tube 12. The "wet out rate" was measured by the distance a particular liquid resin traveled above the upper most surface of the uppermost disk of felt found in the tube 12. The resins designated B-3003/IS, B-3006/IS, and B-3050/IS, are isophthalic polyester resins available from Chemtron International, Inc. of Fresno, Calif. under those designations. XU71867.01 is a vinylester resin also available at Chemtron International, Inc., Fresno, Calif. "Std. Felt" represents polyester teraphthalic felt material having a fineness of 6 denier. The time of each test was (10) minutes. Table I represents the results of these tests:

TABLE I

| TEST | RESIN | RESIN TEMP. °F. | PENETRATION "WET OUT RATE"/CM | NOTES: |
|---|---|---|---|---|
| 1 | B-3003/IS | 40 | 17 | Std. Felt |
| 2 | B-3003/IS | 50 | 18.7 | Std. Felt |
| 3 | B-3003/IS | 60 | 26.0 | Std. Felt |
| 4 | B-3003/IS | 70 | 27.2 | Std. Felt |
| 5 | B-3006/IS | 70 | 2.5 | 1 yr. Old Resin, Std. Felt |
| 6 | B-3006/IS | 70 | 3.9 | Resin Lot 653003, Std. Felt |
| 7 | B-3006/IS | 70 | 0.6 | Resin Lot 652L49 |
| 8 | B-3006/IS | 70 | 26.1 | Resin Lot 653003 Std. Felt |
| 9 | B-3006/IS | 70 | 1.1 | Resin Lot 652L49 Std. Felt |
| 10 | B-3006/IS | 70 | 25.7 | Fresh Resin, Std. Felt |
| 11 | B-3006/is | 70 | 9.3 | Fresh Resin, Std. Felt |
| 12 | B-3006/IS | 70 | 1.6 | Std. Felt |
| 13 | B-3050/IS | 70 | 55 | Std. Felt |
| 14 | XU71867.01 | 77 | 36.5 | Std. Felt |

It is believed that the test showed that, of the isophthalic resins, the B-3050/IS resin penetrated or "wet out" the fastest. The B-3003/IS resin was the next fastest and the B-3006/IS was the slowest of that group. It is also noted that the "wet out rate" was extremely fast for a vinylester resin using standard felt. The above results also indicate large "wet out" variations due to different resin batches and the age of the resin. It is also believed felt of different fineness may be tested for "wet out" ability using identical resin batches.

What is claimed is:

1. An apparatus for determining resin flows through a solid porous material comprising:

a. a tube of a certain cross-sectional size for carrying the resin, said tube including first and second openings;

b. a vessel having an interior chamber, said vessel including an opening for said tube to permit said tube first opening to lie in said chamber of said vessel and said tube second opening to lie outside said chamber;

c. a reservoir for the resin located within said vessel chamber, said tube first opening communicating with the resin in the reservoir;

d. pressure means for urging said resin from said reservoir along said tube toward said second opening of said tube; and e. a mass of the solid porous material placed within the tube between said reservoir and said tube second opening.

2. The apparatus of claim 1 in which said mass of the material comprises a plurality of pieces of the material laid relative to one another.

3. The apparatus of claim 1 which additionally comprises stop means for preventing movement of said mass of the solid porous material within said tube.

4. The apparatus of claim 3 in which said stop means comprises a detent in said tube.

5. The apparatus of claim 1 in which said means for urging said resin from said reservoir along said tube comprises pneumatic means for exerting a pre-determined overpressure on said chamber.

6. The apparatus of claim 5 in which said means for urging said resin from said reservoir along said tube further comprises a vacuum source connected to said second opening of said tube.

7. The apparatus of claim 6 in which said mass of the material comprises a plurality of pieces of the material laid relative to one another.

8. The apparatus of claim 7 which additionally comprises stop means for preventing movement of said mass of the solid porous material within said tube.

9. The apparatus of claim 8 in which said stop means comprises a detent in said tube.

10. A method for determining resin flow through a solid porous material, comprises the steps of:

a. placing a tube, of a certain cross-sectional size and having first and second openings, within an interior chamber of a vessel possessing an opening for said tube;

b. locating a reservoir of the resin within the interior chamber of said vessel;

c. communicating said tube first opening with the resin in the reservoir;

d. providing a mass of the solid porous material within said tube between the reservoir and said tube second opening;

e. urging said resin, by a pre-determined pressure, from said reservoir along said tube toward said mass of the solid porous material; and f. measuring the penetration of said resin relative to said mass of material during a certain period of time.

11. The method of claim 10 which additionally comprises the steps of allowing said resin to harden after said step of measuring the penetration of said resin.

12. The method of claim 10 in which said step of urging said resin by a pre-determined pressure includes the step of applying a vacuum to said second opening of said tube.

* * * * *